United States Patent [19]

Hodek et al.

[11] Patent Number: 4,508,646

[45] Date of Patent: Apr. 2, 1985

[54] PROCESS FOR THE PREPARATION OF A CATALYST USEFUL FOR ANIONIC LACTAM POLYMERIZATION

[75] Inventors: Robert B. Hodek, Gibsonia; Jerome A. Seiner, Pittsburgh, both of Pa.

[73] Assignee: PPG Industries, Inc., Pittsburgh, Pa.

[21] Appl. No.: 575,089

[22] Filed: Jan. 30, 1984

[51] Int. Cl.³ ............................................ C07D 223/10
[52] U.S. Cl. .............................. 260/239.3 R; 546/243; 548/543
[58] Field of Search ................. 260/239.3 R; 546/243; 548/543

[56] References Cited

U.S. PATENT DOCUMENTS

| | | | |
|---|---|---|---|
| 3,018,273 | 1/1962 | Butler et al. | 260/239.3 R |
| 3,450,662 | 6/1969 | Tierney | 260/239.3 R |
| 3,451,963 | 6/1969 | Tierney et al. | 260/239.3 R |
| 4,438,034 | 3/1984 | Garner | 260/239.3 R |

FOREIGN PATENT DOCUMENTS 1167738  10/1969  United Kingdom ......... 260/239.3 R

*Primary Examiner*—Robert T. Bond

*Attorney, Agent, or Firm*—Linda Pingitore

[57] ABSTRACT

An improved process for the preparation of a lactam-magnesium compound which involves bringing into intimate admixture a lactam monomer represented by the following structural formula:

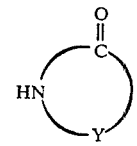

wherein Y is an alkylene group having from 3 to 12 carbon atoms, in particulate form, and an organomagnesium-containing material. The process is carried out at a temperature below the melting point of the lactam monomer but at a temperature sufficient to convert at least a portion of the lactam monomer to said lactam-magnesium compound in pulverulent form. The lactam-magnesium compound is useful as a catalyst for anionic lactam polymerization.

9 Claims, No Drawings

PROCESS FOR THE PREPARATION OF A CATALYST USEFUL FOR ANIONIC LACTAM POLYMERIZATION

BACKGROUND OF THE INVENTION

The present invention relates to the preparation of a lactam-magnesium compound which is useful as a catalyst for anionic lactam polymerization.

It is well known that the anionic polymerization process proceeds most effectively when initiated with a strong basic catalyst. Suitable basic catalysts can be chosen from among a large variety of materials; for example, lactam-metal-containing compounds having an alkali metal atom bound to the nitrogen atom. One particularly useful class of these lactam-metal-containing materials are lactam-magnesium compounds such as capro-lactam magnesium bromide.

Heretofore, these lactam-magnesium compounds have been prepared either by a process which requires heating of the lactam monomer and the organomagnesium material at elevated temperatures for an extended period in order to melt the lactam monomer, or by dissolving the lactam monomer in a solvent. These procedures are not without attendant difficulties. For example, heating of the lactam at an elevated temperature increases the probability that the lactam monomer will polymerize. Moreover, even when the process is successfully carried out, the catalyst product generally requires further mechanical processing such as grinding prior to use. Although dissolving the lactam monomer in a solvent prior to reaction with the organomagnesium-containing material saves energy because the need for heating of the lactam monomer to melt it is alleviated, the catalyst product still requires mechanical processing prior to use.

There is a need, therefore, for an improved method of preparing anionic polymerization catalysts which is simple, efficient, and economical and results in a product which can be utilized without mechanical processing prior to use.

SUMMARY OF THE INVENTION

In accordance with the present invention, there is provided an improved process for the preparation of a lactam-magnesium compound. In a process for the preparation of a lactam-magnesium compound comprising reacting lactam monomer with an organomagnesium-containing material, the improvement comprises bringing the lactam monomer in particulate form into intimate admixture with the organomagnesium-containing material at a temperature below the melting point of the lactam monomer but at a temperature sufficient to convert at least a portion of lactam represented by the following structural formula:

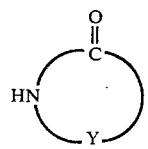

wherein Y is an alkylene group having from 3 to 12 carbon atoms monomer to said lactam-magnesium compound in pulverulent form.

DETAILED DESCRIPTION OF THE INVENTION

Broadly stated, the process of the present invention comprises bringing together into intimate admixture a lactam monomer in particulate form and an organomagnesium-containing material. The aforesaid components are brought together at a temperature below the melting point of the lactam monomer but at a temperature sufficient to convert at least a portion of the lactam monomer to lactam-magnesium compound in pulverulent form.

Suitable lactam monomers can be represented by the following structural formula

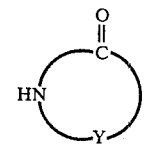

wherein Y is an alkylene group having from 3 to 12 carbon atoms. Examples of suitable lactams include butyrolactam, valerolactam, epsilon-caprolactam, laurolactam, 2-pyrrolidinone, and 2-azocyclotridecanone. Preferably, epsilon-caprolactam is utilized. The lactam monomer which is utilized in the claimed process is in particulate form. In the event that the desired lactam monomer is not normally in particulate form, e.g. a liquid, it can nevertheless be utilized in the claimed process. The liquid lactam monomer can be readily converted to particulate form by, for example, freezing and then pulverizing the resultant solid.

The organomagnesium-containing material is preferably an organomagnesium halide. Exemplary of these preferred materials are Grignard reagents. Suitable Grignard reagents include a large variety of materials which are commercially available, for example, allyl magnesium chloride; benzyl magnesium chloride; n-butyl magnesium chloride; sec-butyl magnesium chloride; p-chlorophenyl magnesium chloride, cyclohexyl magnesium chloride, ethyl magnesium chloride, isopropyl magnesium chloride, methyl magnesium chloride, phenyl magnesium chloride, n-propyl magnesium chloride, otolyl magnesium chloride, vinyl magnesium chloride; ethyl magnesium bromide, methyl magnesium bromide and n-octyl magnesium chloride. Preferably, ethyl magnesium bromide, benzyl magnesium chloride, and methyl magnesium bromide are utilized. Other organomagnesium-containing materials such as dibutyl magnesium are also useful herein. The Grignard reagants utilized herein are usually in the presence of ether or other solvent.

The particulate lactam monomer and organomagnesium-containing material are brought into intimate admixture at a temperature below the melting point of the lactam monomer but at a temperature sufficient for reaction between the lactam monomer and the organomagnesium-containing material. For example, when epsilon-caprolactam is utilized as the lactam monomer, the temperature is generally at least 0° C. Usually, however, the process of the present invention is carried out at ambient temperature. Admixture is typically accomplished by vigorously agitating the materials together by means of a mechanical stirring or propelling device. The resultant reaction mixture is a heterogenous phase mixture. The reaction is believed to be complete and the pulverulent lactam-magnesium compound formed upon termination of the exotherm which results upon admixture of the organomagnesium-containing material and the particulate lactam monomer. The process of the present invention can be termed a "solid state" preparation since the process is carried out without solubilizing or melting the lactam monomer. That is, the lactam monomer participates in the reaction as a solid without proceeding through a fluid state. It should be understood that this is the case even though the Grignard reagent is usually associated with ether or other solvent. The amount of ether or other solvent associated with the Grignard reagent is inadequate to solubilize the lactam monomer.

The term "solid state" also encompasses the embodiment of the present invention wherein the particulate lactam monomer is in essentially dispersed form in a diluent prior to admixture with the organomagnesium-containing material. In this embodiment the diluent is preferably a material with low solubility for the monomer and final lactam-magnesium compound. Materials which are essentially non-solvents for the lactam monomer are preferred as diluents. Examples of suitable non-solvents include aliphatic hydrocarbons such as cyclopentane, cyclohexane, hexane, and heptane. Preferably, aliphatic hydrocarbons such as cyclohexane are utilized herein. Exemplary of suitable catalysts prepared according to present invention are caprolactam magnesium bromide, laurolactam magnesium bromide, and caprolactam magnesium chloride.

The quantities of particulate lactam monomer and organomagnesium-containing material, preferably Grignard reagent which are utilized in the claimed process can vary depending upon the amount of theoretical conversion desired. That is, the amount, on a mole percent basis, of lactam monomer converted to lactam-magnesium compound. Generally one mole of lactam monomer will react with one mole of organomagnesium-containing material to form the resultant lactam-magnesium compound. Quantities can be selected to yield theoretical conversions of up to 100 mole percent. Typically, however, quantities are selected to yield theoretical conversions ranging from 15 mole percent to 50 mole percent. For example, in one embodiment, 100 moles of epsilon-caprolactam is reacted with 50 moles of ethyl magnesium bromide resulting in a theoretical conversion of 50 mole percent. Depending upon the percentage conversion, the resultant pulverulent catalyst will have a corresponding quantity of unreacted particulate lactam monomer associated with it. The presence of this monomer does not detract from the properties of the lactam-magnesium-containing anionic catalyst but rather in some instances, it is believed to facilitate handling.

In the embodiment of the present invention wherein the particulate lactam monomer is in essentially dispersed form, preferably in a non-solvent, prior to admixture with the organomagnesium-containing material, the volume of non-solvent is adjusted to permit thorough mixing and agitation of the resultant dispersion.

Since the process of the present invention is conducted below the melting point of the lactam monomer and the molten conditions of the prior art are avoided the potential of lactam polymerization is reduced. Moreover, since the product is in the form of a dusty powder, it is directly usable without the necessity for further mechanical processing such as grinding. The claimed process is efficient, economical, and results in a pulverulent product with good catalytic activity and immediate usability without further processing.

The invention will be further described in connection with the examples which follow. These examples are given as illustrative of the invention and are not to be construed as limiting it to their details.

EXAMPLE I

This Example illustrates the preparation of an anionic catalyst for lactam polymerization according to the present invention.

| Ingredients | Amount |
| --- | --- |
| epsilon-caprolactam | 150 grams |
| ethyl magnesium bromide (2.9 M in ether) | 92 milliliters |

The ethyl magnesium bromide was added to the epsilon-caprolactam in thirty milliliter aliquots over a period of an hour at a temperature of 32° C. After the addition was complete, the reaction product was vacuum stripped leaving the caprolactam magnesium bromide catalyst as a pulverulent residue. The theoretical conversion of lactam monomer to catalyst was 20 mole percent.

EXAMPLE II

This Example also illustrates the preparation of an anionic catalyst for lactam polymerization according to the present invention. In the embodiment represented by this Example, the lactam monomer is dispersed in cyclohexane prior to admixture with the organomagnesium halide.

| Ingredients | Amount |
| --- | --- |
| epsilon-caprolactam | 125 grams |
| cyclohexane | 475 grams |
| ethyl magnesium bromide | 76.3 milliliters |

The epsilon-caprolactam was agitated together with the cyclohexane until a dispersion was formed. Subsequently, the ethyl magnesium bromide was added in 20 milliliter aliquots at such a rate that the reaction temperature was maintained below 45° C. After each aliquot addition, the mixture was placed in vacuo for five minutes. After the final aliquot addition, the cyclohexane was removed in vacuo leaving the caprolactam magnesium bromide catalyst as a white pulverulent residue. The theoretical conversion of lactam monomer to catalyst in this example was also 20 mole percent.

EXAMPLE III

This Example is similar to Example II, above, with the exception that benzyl magnesium chloride was used in place of ethyl magnesium chloride.

| Ingredients | Amount |
| --- | --- |
| epsilon-caprolactam | 113 grams |
| cyclohexane | 500 grams |
| benzyl magnesium chloride (2 M in tetra hydrofuran) | 100 milliliters |

The epsilon-caprolactam was agitated together with 400 grams of the cyclohexane until a dispersion was formed. Subsequently, the benzyl magnesium chloride was added in 25 milliliter aliquots. After each aliquot addition the mixture was placed in vacuo for five minutes. After the final aliquot, an additional 100 grams of cyclohexane was added and the reaction mixture placed in vacuo to remove the cyclohexane leaving the caprolactam magnesium chloride catalyst as a pulverulent residue. The theoretical conversion of lactam monomer to catalyst in this example was also 20 mole percent.

EXAMPLE IV

This Example is similar to Example II, above, with the exception that the theoretical conversion of lactam monomer to catalyst was 50 mole percent.

| Ingredients | Amount |
| --- | --- |
| epsilon-caprolactam | 100 grams |
| cyclohexane | 500 grams |
| ethyl magnesium bromide (2.9M in ether) | 152.6 milliliters |

The epsilon-caprolactam was agitated together with the cyclohexane until a dispersion was formed. Subsequently, the ethyl magnesium bromide was added in 25 milliliter aliquots. After each aliquot addition, the mixture was placed in vacuo for five minutes. After the final aliquot addition, the reaction mixture was held for two hours under a nitrogen blanket and then placed in vacuo to remove the cyclohexane. The resultant pulverulent residue was the caprolactam magnesium bromide catalyst.

EXAMPLE V

This Example is similar to Example I, above, with the exception that laurolactam was used instead of epsilon-caprolactam.

| Ingredients | Amount |
| --- | --- |
| laurolactam | 180 grams |
| ethyl magnesium bromide (2.85M in ether) | 64 milliliters |

The ethyl magnesium bromide was added to the laurolactam continuously over a period of an hour at a temperature of 32° C. After the addition was complete, the reaction product was vacuum stripped leaving the laurolactam magnesium bromide catalyst as a pulverulent residue. The theoretical conversion of lactam monomer to catalyst was 20 mole percent.

What is claimed is:

1. In a process for the preparation of a lactam-magnesium compound comprising reacting lactam monomer with an organomagnesium-containing material, the improvement comprises bringing lactam monomer represented by the following structural formula:

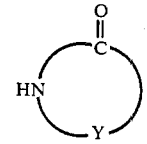

wherein Y is an alkylene group having from 3 to 12 carbon atoms, in particulate form, into intimate admixture with the organomagnesium-containing material at a temperature below the melting point of the lactam monomer but at a temperature sufficient to convert at least a portion of the lactam monomer to said lactam-magnesium compound in pulverulent form.

2. The process of claim 1 wherein the admixture is carried out at or about ambient temperature.

3. The process of claim 1 wherein the lactam monomer is in essentially dispersed form in a diluent prior to admixture with the organomagnesium-containing material.

4. The process of claim 3 wherein the diluent is an aliphatic hydrocarbon.

5. The process of claim 4 wherein the diluent is cyclohexane.

6. The process of claim 1 wherein the lactam monomer is epsilon-caprolactam.

7. The process of claim 1 wherein the organomagnesium containing material is an organomagnesium halide.

8. The process of claim 7 wherein the organomagnesium halide is selected from ethyl magnesium bromide and benzyl magnesium chloride.

9. The process of claim 1 wherein the lactam magnesium compound is caprolactam magnesium bromide.

* * * * *